United States Patent [19]

Song et al.

[11] Patent Number: 5,534,641
[45] Date of Patent: Jul. 9, 1996

[54] ACETYLENES DISUBSTITUTED WITH 2-TETRAHYDROPYRANOXYARYL AND ARYL OR HETEROARYL GROUPS HAVING RETINOID-LIKE BIOLOGICAL ACTIVITY

[75] Inventors: Tae K. Song, Long Beach; Roshantha A. Chandraratna, Mission Viejo, both of Calif.

[73] Assignee: Allergan

[21] Appl. No.: 366,173

[22] Filed: Dec. 29, 1994

[51] Int. Cl.$^6$ .................................................. C07D 309/12
[52] U.S. Cl. ........................... 549/416; 549/419; 549/60; 546/282.1; 544/333; 544/405; 544/238; 548/235; 548/204; 548/236
[58] Field of Search ..................................... 549/416, 419

[56] References Cited

FOREIGN PATENT DOCUMENTS 2231454   9/1990   Japan .

Primary Examiner—Jane Fan
Attorney, Agent, or Firm—Gabor L. Szekeres; Robert J. Baran; Martin A. Voet

[57] ABSTRACT

Compounds of the formula

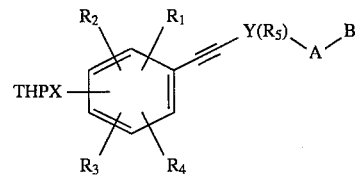

wherein $R_1$–$R_5$, X, Y, A, B are as defined in the specification have retinoid-like biological activity.

21 Claims, No Drawings

ACETYLENES DISUBSTITUTED WITH 2-TETRAHYDROPYRANOXYARYL AND ARYL OR HETEROARYL GROUPS HAVING RETINOID-LIKE BIOLOGICAL ACTIVITY

FIELD OF THE INVENTION

The present invention relates to novel compounds having retinoid-like activity. More specifically, the present invention relates to compounds having an acetylene portion which is substituted with a 2-tetrahydropyranoxyaryl group and by a substituted aryl or substituted heteroaryl group having an acid function. The acid function may also be converted to an alcohol, aldehyde or ketone or derivatives thereof, or may be reduced to —$CH_3$.

BACKGROUND ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. Nos. 5,013,744, 5,175,185 and 5,264,456 disclose acetylene compounds which are substituted by an alkylphenyl, alkoxyphenyl or thioalkoxyphenyl group and by a heteroaryl carboxylic acid or carboxylic acid ester group, having retinoid-like biological activity.

Several co-pending applications, which are assigned to the assignee of the present application, are directed to further compounds having retinoid-like activity.

SUMMARY OF THE INVENTION

The present invention covers compounds of Formula 1

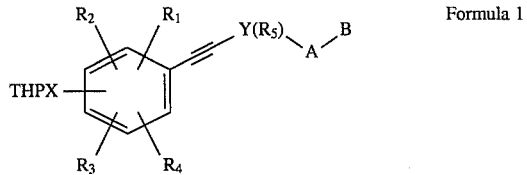

Formula 1 wherein $R_1$–$R_5$ independently are hydrogen, lower alkyl of 1 to 6 carbons, branched chain alkyl or cycloalkyl of 3 to 15 carbons, lower alkyl substituted cycloalkyl of 3 to 15 carbons;

THP is a 2-tetrahydropyranyl group;

X is S or O;

Y is a phenyl group, or heteroaryl selected from a group consisting of pyridyl, thienyl, furyl, pyridazinyl, pyrimidinyl, pyrazinyl, thiazolyl and oxazolyl, said groups being substituted with the $R_5$ group defined above;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R10$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3, where $X_1$ is halogen, B' is H, or a protected acid, alcohol, aldehyde, or ketone, in the presence of cuprous iodide and $Pd(PQ_3)_2Cl_2$ (Q is phenyl) or a similar complex, or reacting the zinc salt of the compound shown in Formula 2 with a compound of Formula 3 in the presence of $Pd(PQ_3)_4$ (Q is phenyl) or similar complex. In the alternative, this invention relates to the process for making a compound of Formula 1 which process comprises reacting a compound of Formula 4 with a compound of Formula 5, where the symbols are defined as in connection with Formula 2 and Formula 3, in the presence of cuprous iodide and $Pd(PQ_3)_2Cl_2$ (Q is phenyl) or a similar complex, or reacting the zinc salt of the compound shown in Formula 5 with a compound of Formula 4 in the presence of Pd(PQ₃)₄ (Q is phenyl) or similar complex.

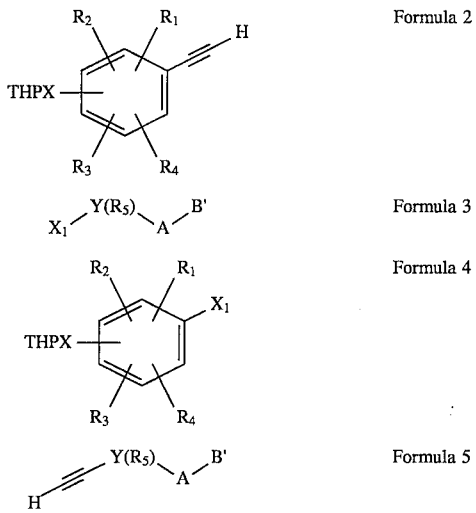

Formula 2

Formula 3

Formula 4

Formula 5

Still further, the present invention relates to such reactions performed on the compounds of Formula 1 which cause transformations of the A–B group while the reaction product still remains within the scope of Formula 1.

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 5 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH₂OH, this term covers compounds derived from organic acids capable of forming esters including phosphorous based and sulfur based acids, or compounds of the formula —CH₂OCOR₁₁ where R₁₁ is any substituted or unsubstituted aliphatic, aromatic, heteroaromatic or aliphatic aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula —CK where K is (—OR)₂. Here, R is lower alkyl. Also, K may be —OR₇O— where R₇ is lower alkyl of 2–5 carbon atoms, straight chain or branched.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalention. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds utilized in accordance with the present invention may have trans and cis (E and Z) isomers. In addition, the compounds of the present invention contain one (and may contain more than one) chiral center and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbol Y in Formula 1, the preferred compounds of the invention are those where Y is phenyl, pyridyl, thienyl or furyl. Even more preferred are compounds where Y is phenyl or pyridyl. As far as substitutions on the Y (phenyl) and Y (pyridyl) groups are concerned, compounds are preferred where the phenyl group is 1,4 (para) substituted, and where the pyridine ring is 2,5 substituted. (Substitution in the 2,5 positions in the "pyridine" nomenclature corresponds to substitution in the 6-position in the "nicotinic acid" nomenclature.) The R₅ group of the aromatic ring Y is preferably hydrogen.

With reference to the symbol X in Formula 1, compounds are preferred in accordance with the invention where X is oxygen. In the preferred compounds of the invention the substituents R₁–R₄ may all be hydrogen. Alternatively, compounds are preferred where three (say R₁–R₃) of the four possible substituents are hydrogen, and the fourth one (R₄) is other than hydrogen. In this regard compounds are preferred in accordance with the invention where R₄ is branched chain alkyl, or 1-adamantyl. When the only substituents on the phenyl ring are the tetrahydropyranoxy group and the ethynyl group (R₁–R₄ all are hydrogen) then the preferred substitution patterns are 1,4 (para) and 1,3 (meta). When including the tetrahydropyranoxy group and the ethynyl group there are three substituents on the phenyl ring (R₄ is not hydrogen) then the preferred substitution patterns are 1,2,4 and 1,2,5 with the tetrahydropyranoxy group occupying the 1-position, $R_4$ occupying the 2-position and the ethynyl group occupying the 4- or the 5-position.

Referring now to the A–B group of Formula 1, compounds are preferred in accordance with the invention where A is $(CH_2)_n$ where n is 0 to 3, and even more preferred where n is 0. B is preferably COOH (carboxylic acid or salt thereof), $COOR_8$ (ester), or $CONR_9R_{10}$ (amide).

The most preferred compounds of the invention are listed in Table 1 with reference to Formulas 6 and 7.

TABLE 1

| Compound # | Formula # | $R_4$ | $X_2$ | $R_8$ |
|---|---|---|---|---|
| 1 | 6 | t-butyl | CH | ethyl |
| 2 | 6 | t-butyl | CH | H |
| 3 | 6 | t-butyl | N | ethyl |
| 4 | 6 | t-butyl | N | H |
| 5 | 7 | t-butyl | N | ethyl |
| 6 | 7 | t-butyl | CH | ethyl |
| 7 | 7 | t-butyl | CH | H |
| 8 | 7 | t-butyl | N | H |
| 9 | 6 | admtyl[1] | CH | ethyl |
| 12 | 6 | admtyl[1] | CH | H |
| 15 | 6 | H | N | H |
| 16 | 7 | H | N | ethyl |
| 17 | 7 | admtyl[1] | N | ethyl |
| 18 | 7 | admtyl[1] | CH | ethyl |
| 19 | 7 | admtyl[1] | N | H |
| 21 | 7 | H | CH | H |
| 24 | 7 | H | CH | ethyl |
| 25 | 6 | admtyl[1] | CH | methyl |

[1]admtyl = 1-adamantyl

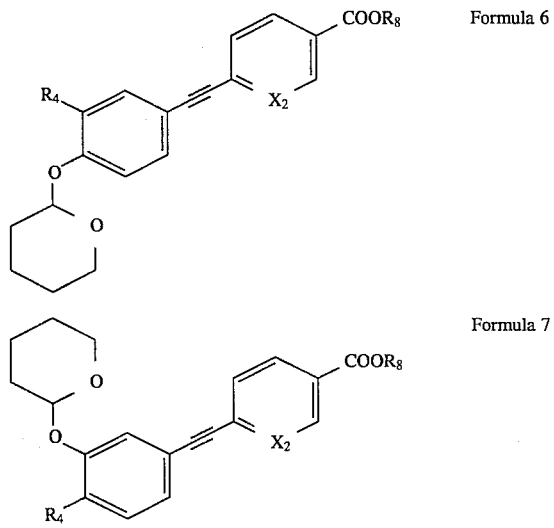

Formula 6

Formula 7

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, ache, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the abovedescribed ODC assay is disclosed in Table 2 which provides either $IC_{80}$ (or other measured per cent inhibition at the indicated concentration) for the respective exemplary compound. ("$IC_{80}$" is that concentration of the test compound which causes 80% inhibition in the ODC assay; by analogy, e.g. $IC_{52}$ is that concentration which causes 52% inhibition.)

TABLE 2

| Compound # (nmol) | IC$_{80}$ conc (nmols) | % of inhib | conc |
|---|---|---|---|
| 1 | 6.30 | — | |
| 2 | 0.84 | — | |
| 3 | 5.40 | — | |
| 4 | <3 | — | |
| 5 | 0.56 | — | |
| 6 | 0.70 | — | |
| 7 | 2.90 | — | |
| 8 | 5.20 | — | |
| 9 | — | 49 | 30 |
| 12 | 6.80 | — | |
| 15 | — | 44 | 300 |
| 16 | — | 52 | 300 |
| 17 | — | 68 | 300 |
| 18 | — | 45 | 300 |
| 19 | — | 45 | 300 |
| 21 | 58.00 | — | |
| 24 | 38.00 | — | |
| 25 | — | 61 | 30 |

Specific Embodiments

The compounds of this invention can be made by the synthetic chemical pathways illustrated here. The synthetic chemist will readily appreciate that the conditions set out here are specific embodiments which can be generalized to any and all of the compounds represented by Formula 1.

compound of Formula 9, to yield the substituted bromophenols of Formula 10. The bromophenols of Formula 9 are commercially available. Moreover, several substituted (such as alkylated) bromophenols within the scope of Formula 10 are also available commercially, thereby rendering the compounds of Formula 10 readily accessible to one of ordinary skill in the art as commercially available chemicals and/or through use of such Fridel Crafts alkylation (and the like) reactions which are well known in the art.

Referring still to Reaction Scheme 1, the compounds of Formula 10 are then reacted with 3,4-dihydro-2H-pyran (DHP) to provide the 2-tetrahydropyranoxy bromobenzenes of Formula 11. The latter reaction is typically conducted in an inert aprotic solvent, such as dichloromethane (CH$_2$Cl$_2$), under mildly acidic conditions, such as in the presence of pyridinium p-tolunesulfonate (PPTS). The 2-tetrahydropyranoxy bromobenzenes of Formula 11 are thereafter reacted with trimethylsilylacetylene to provide the 2-tetrahydropyranoxy trimethylsilylethynylbenzenes of Formula 12. The reaction with trimethylsilylacetylene is typically conducted at moderate heat (55°–70° C.) in the presence of cuprous iodide, a suitable catalyst, typically having the formula Pd(pph$_3$)$_2$Cl$_2$, an acid acceptor (such as diethylamine) under an inert gas (argon) atmosphere. The 2-tetrahydropyranoxy trimethylsilylethynylbenzenes of Formula 12 are then reacted with base (potassium hydroxide or potassium carbonate) in an alcoholic solvent, such as methanol, to provide

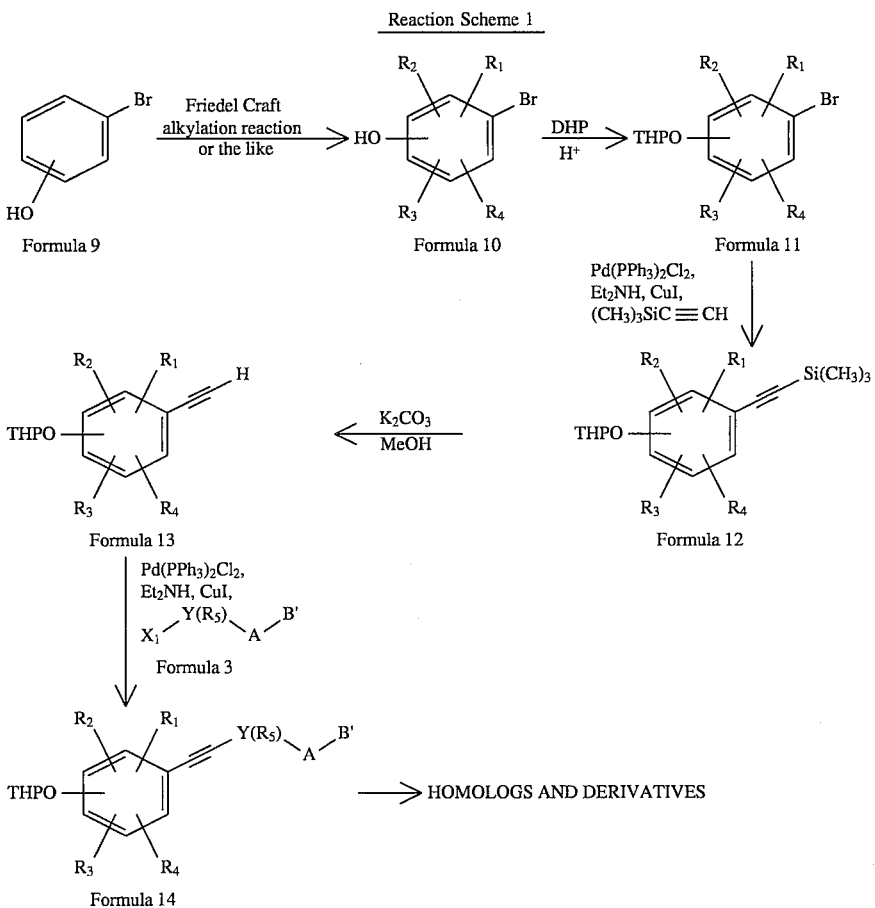

Reaction Scheme 1

In accordance with Reaction Scheme 1, the appropriate substituent groups R$_1$–R$_4$ are introduced by one or more Friedel-Crafts (or the like) reactions into the bromophenol the tetrahydropyranoxy ethynylbenzenes of Formula 13. The ethynyl compounds of Formula 13 are preferably coupled directly with the aromatic or heteroaromatic reagent $X_1$—$Y(R_5)$—A—B' (Formula 3) in the presence of cuprous iodide, a suitable catalyst, typically $Pd(PPh_3)_2Cl_2$, an acid acceptor, such as diethylamine, under inert gas (argon) atmosphere. Alternatively, a zinc salt (or other suitable metal salt) of the compounds of Formula 13 can be coupled with the reagents of Formula 3 in the presence of $Pd(PPh_3)_4$ or similar complex. Generally speaking, coupling between an ethynylbenzene compound or its zinc salt and a halogen substituted aryl or heteroaryl compound, such as the reagent of Formula 3, are described in U.S. Pat. No. 5,264,456, the specification of which is expressly incorporated herein by reference. The compounds of Formula 14 are the compounds of the invention, or a derivative thereof protected in the B' group, from which the protecting group can be readily removed by reactions well known in the art. The compounds of Formula 14 can also be converted into further compounds of the invention by such reactions and transformations which are well known in the art. Such reactions are indicated in Reaction Scheme 1 by conversion into "homologs and derivatives". One such conversion employed for the synthesis of several exemplary compounds of this invention is saponification of an ester group (when B or B' is an ester) to provide the free carboxylic acid or its salt.

The halogen substitituted aryl or heteroaryl compounds of Formula 3 can, generally speaking, be obtained by reactions well known in the art. An example of such compound is ethyl 4-iodobenzoate which is obtainable, for example, by esterification of 4-iodobenzoic acid. Another example is ethyl 6-iodonicotinate which can be obtained by conducting a halogen exchange reaction on 6-chloronicotinic acid, followed by esterification. Even more generally speaking regarding derivatization of compounds of Formula 14 and/or the synthesis of aryl and heteroaryl compounds of Formula 3 which can thereafter be reacted with compounds of Formula 13 to yield compound of the invention, the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n in the compounds of Formula 3 before affecting the coupling reaction of Reaction Scheme 1 (where such compounds corresponding to Formula 3 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of Formula 3, (or of Formula 1 or of Formula 14) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 3 (or of Formula 1 or of Formula 14) where the A group has a triple (acetylenic) bond can be made by reaction of a corresponding aromatic-methyl ketone with strong base, such as lithium diisopropyl amide.

The acids and salts derived from compounds of Formula 14 (or of Formula 1) are readily obtainable from the corresponding esters. Basic saponification with an alkali metal base will provide the acid. For example, an ester of Formula 14 (or of Formula 1) may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 3 (or of Formula 14 or of Formula 1) where B is H can be prepared from the corresponding halogenated aromatic or hetero aromatic compounds, preferably where the halogen is I.

Compounds of Formula 1 where X is sulfur can be prepared in the manner described above in connection with Reaction Scheme 1 but utilizing, instead of a bromophenol (Formula 9), an analogous bromothiophenol.

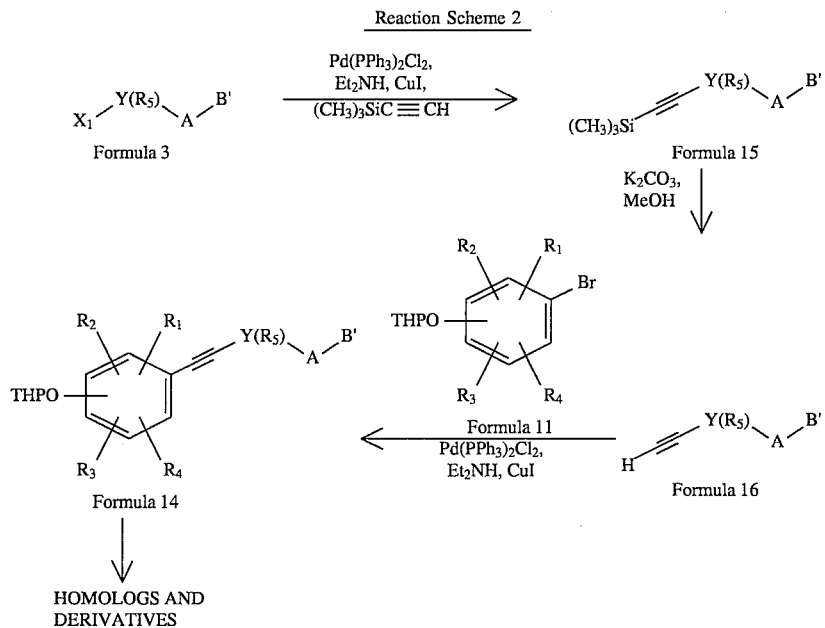

Reaction Scheme 2 illustrates another example of a synthetic procedure for preparing compounds of Formula 14, and by analogy all compounds of Formula 1. In accordance with this scheme, the halogenated aromatic or heteroaromatic compound of Formula 3 is reacted with trimethylsilyl acetylene to yield the compounds of Formula 15. As in the analogous reaction described in Reaction Scheme 1, the reaction with trimethylsilylacetylene is typically conducted at moderate heat in the presence of cuprous iodide, a suitable catalyst, typically having the formula Pd(PPh$_3$)$_2$Cl$_2$, an acid acceptor (such as diethylamine) under an inert gas (argon) atmosphere. The trimethylsilyl group is removed from the ethyne function of the compounds of Formula 15 by treatment with base, preferably anhydrous potassium hydroxide, in an alcoholic solvent, such as methanol, to yield the aryl or heteroaryl ethyne compounds of Formula 16. The ethyne compounds of Formula 16 are coupled with the 2-tetrahydropyranoxy bromobenzenes of Formula 11 in the presence of cuprous iodide, a suitable catalyst, typically Pd(PPh$_3$)$_2$Cl$_2$, an acid acceptor, such as diethylamine, under inert gas (argon) atmosphere, to yield compounds of Formula 14. Alternatively, a zinc salt (or other suitable metal salt) of the compounds of Formula 16 can be coupled with the reagents of Formula 11 in the presence of Pd(PPh$_3$)$_4$ or similar complex. These conditions are similar to the conditions of coupling of compounds of Formula 3 with compounds of Formula 13 described above in connection with Reaction Scheme 1. The compounds of Formula 14 can be the biologically active compounds of the invention, or can be converted into such compounds by removal of protecting group or groups (as in the group B'), or can be converted into further biologically active homologs and derivatives.

The following examples of specific compounds of the invention, and specific examples of the synthetic steps in which the compounds and certain intermediates are made, are set out to illustrate the invention, not to limit its scope.

SPECIFIC EXAMPLES

Ethyl 4-iodobenzoate (Compound A)

To a suspension of 24.9 g (100.4 mmol) of 4-iodobenzoic acid in 46.25 g (58.9 ml, 1.0 mol) of ethanol (100%) was added 3.0 ml of conc. sulfuric acid. The resulting mixture was refluxed for 60 minutes, and then distilled until a clear, homogeneous solution was obtained. The solution was allowed to cool to room temperature, partitioned between 250 ml of water and 250 ml of pentane, and the layers were separated. The aqueous phase was washed with 3×100 ml-portions of pentane. All organic phases were combined, washed with brine solution, dried over MgSO$_4$, filtered and concentrated in vacuo to a dark yellow oil. Purification by flash chromatography (silica, 10% ethyl acetate in hexane) yielded the title compound as a clear, light yellow oil. PMR (CDCl$_3$):d 1.39 (3H, t, J=7.2 Hz), 4.37 (2H, q, J=7.2 Hz), 7.73–7.82 (4H, m).

6-Iodonicotinic acid (Compound B)

To 27.97 g (186.6 mmol) of sodium iodide cooled to −78° C. was added 121.77 g (71.6 ml, 952.0 mmol) of hydriodic acid (in 57 wt % aqueous solution). The reaction mixture was allowed to warm slightly with stirring for 5 minutes and then 30.00 g (190.4 mmol) of 6-chloronicotinic acid was added. The resulting mixture was allowed to warm to room temperature with stirring and then heated at 120°–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1 N aqueous NaHSO$_3$ solution, and dried in vacuum (3 mm Hg) to give the title compound as a pale yellow solid. PMR (DMSO-d$_6$):d 7.90 (1H, dd, J=8.1, 2 Hz), 7.99 (1H, d, J=8.1 Hz), 8.80 (1H, d, J=2 Hz).

Ethyl 6-iodonicotinate (Compound C)

To a suspension of 23.38 g (94.2 mmol) of 6-iodonicotinic acid (Compound B) in 100 ml of dichloromethane was added a solution of 19.86 g (103.6 mmol) of 1-(3-dimethylaminopropyl)-3-ethylcarbodiimide hydrochloride in 250 ml of dichloromethane. To this suspension was added 12.40 g (15.8 ml, 269.3 mmol) of ethanol (100%) and 1.15 g (9.4 mmol) of 4-dimethylaminopyridine. The resulting solution was then heated at 50° C. in an oil bath for 24.5 hours, concentrated in vacuo, partitioned between 200 ml of water and 250 ml of ethyl ether, and the layers were separated. The aqueous phase was washed with 2×150 ml-portions of ethyl ether. All organic phases were combined, washed with 75 ml of brine solution, dried over $MgSO_4$, filtered and concentrated in vacuo to give a yellow solid. Purification by flash chromatography (silica, 10% ethyl acetate in hexane) yielded the title compound as white needles. PMR ($CDCl_3$):d 1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

5-Bromo-2-t-butylphenol (Compound D)

To a solution of 29.46 g (170.3 mmol) of 3-bromophenol (distilled) and 16.41 g (20.9 ml, 221.3 mmol) of t-butanol in 100 ml of carbon tetrachloride was added 20.0 ml of conc. sulfuric acid. The clear, colorless solution turned a dark magenta color and became hot. The solution was cooled in water (ambient temperature) and allowed to stir at room temperature for 84 hours. The reaction mixture was neutralized with sat. aqueous $NaHCO_3$ solution (pH ~7.0), partitioned between 300 ml of water and 500 ml of dichloromethane, and the organic and aqueous layers were separated. The aqueous phase was washed with 2×500 ml-portions of dichloromethane. All organic phases were combined, washed with 400 ml of brine solution, dried over $MgSO_4$, filtered and concentrated in vacuo to a purple oil. Purification by flash chromatography (silica, 5% ethyl acetate in hexane) followed by kugelrohr distillation yielded the title compound as a clear, slightly yellow oil.

PMR ($CDCl_3$):d 1.37 (9H, s), 4.89 (1H, s), 6.83 (1H, d, J=2.0 Hz), 6.99 (1H, dd, J=8.5, 2.0 Hz), 7.12 (1H, d, J=8.5 Hz).

4-Bromo-2-t-butylphenol (Compound E)

Using the same general procedure as for the preparation of 5-bromo-2-t-butylphenol (Compound D), but instead using 50.00 g (289.0 mmol) of 4-bromophenol, 21.40 g (27.25 ml, 289.0 mmol) of t-butanol, 14.0 ml of conc. sulfuric acid (added slowly) and 140 ml of distilled carbon tetrachloride, stirred at room temperature for 24 hours produced a dull green-colored solution and a white precipitate. At this time an additional 3.5 ml of conc. sulfuric acid was added and the solution was allowed to stir for 4 days at room temperature. After aqueous workup, a dark yellow oil was isolated. Purification by flash chromatography (silica, 2% ethyl acetate in hexane) yielded the title compound as a clear, light yellow oil. PMR ($CDCl_3$):d 1.38 (9H, s), 4.79 (1H, s), 6.54 (1H, d, J=8.5 Hz), 7.16 (1H, dd, J=8.5, 2.5 Hz), 7.35 (1H, d, J=2.5 Hz).

2-(1-adamantyl)-4-bromophenol (Compound F)

To a suspension of 6.92 g (40.0 mmol) of 4-bromophenol and 6.08 g (40.0 mmol) of 1-adamantanol in 20 ml of dichloromethane (anhydrous) was added 2.0 ml of conc. sulfuric acid over a span of 2 minutes. The solution became orange in color and a white precipitate was formed. The solution was allowed to stir at room temperature for 8 hours, partitioned between 250 ml of water and 100 ml of ethyl ether, diluted with approximately 60 ml of sat. aqueous $NaHCO_3$ solution and allowed to stir at room temperature. The layers were separated and the aqueous phase was washed with 3×75 ml-portions of dichloromethane. All organic phases were combined, dried over $MgSO_4$, filtered and concentrated in vacuo to yield a yellow solid. Purification by flash chromatography (silica, 10% ethyl acetate in hexane) yielded the title compound as a light yellow solid. PMR ($CDCl_3$):d 1.77 (6H, s), 2.08 (9H, s), 4.76 (1H, s), 6.53 (1H, d, J= 8.4 Hz), 7.14 (1H, dd, J= 8.4, 2.4 Hz), 7.29 (1H, d, J= 2.4 Hz).

2-(1-adamantyl)-5-bromophenol (Compound G)

Using the same general procedure as for the preparation of 2-(1-adamantyl)-5-bromophenol (Compound F), but instead using 14.05 g (81.2 mmol) of 3-bromophenol (distilled), 12.36 g (81.2 mmol) of 1-adamantanol and 5.0 ml of conc. sulfuric acid (added in several portions over a 5 minute period) and 50 ml of dichloromethane gave an orange solid. Purification by flash chromatography (silica, 5% ethyl acetate in hexane) yielded the title compound as a white solid. PMR ($CDCl_3$): d 1.77 (6H, s), 2.07 (9H, s), 4.82 (1H, s), 6.82 (1H, d, J= 1.9 Hz), 7.01 (1H, dd, J= 8.4, 1.9 Hz), 7.06 (1H, d, J= 8.4 Hz).

4-Bromo-2-t-butyl-1-(2-tetrahydropyranoxy)benzene (Compound H)

To a solution of 18.92 g (82.6 mmol) of 4-bromo-2-t-butylphenol (Compound E) in 110 ml of dichloromethane was added dropwise 10.42 g (11.3 ml, 123.9 mmol) of 3,4-dihydro-2H-pyran. To this clear, colorless solution was added 1.86 g (7.4 mmol) of pyridinium p-toluenesulfonate. The resulting mixture was stirred at room temperature under a blanket of argon for 26.5 hours, partitioned between 250 ml of water and 400 ml of hexane, and the layers were separated. The organic phase was washed with 2×250 ml-portions of water and 150 ml of brine solution, dried over $MgSO_4$, filtered and concentrated in vacuo to a yellow oil. Purification by flash chromatography (silica, 5% ethyl acetate in hexane) yielded the title compound as a light yellow, crystalline solid. PMR ($CDCl_3$):d 1.39 (9H, s), 1.6–2.1 (6H, m), 3.6–3.7 (1H, m), 3.8–3.9 (1H, m), 5.43 (1H, t, J= 2.7 Hz), 7.06 (1H, d, J= 8.8 Hz), 7.24 (1H, dd, J= 8.8, 2.7 Hz), 7.36 (1H, d, J= 2.7 Hz).

5-Bromo-2-t-butyl-1-(2-tetrahydropyranoxy)benzene (Compound I)

Using the same general procedure as for the preparation of 4-bromo-2-t-butyl-1-(2-tetrahydropyranoxy)benzene (Compound H), but instead using 8.18 g (35.7 mmol) of 5-bromo-2-t-butylphenol (Compound D), 0.90 g, 3.6 mmol) of pyridinium p-toluenesulfonate and 4.50 g (4.9 ml, 53.6 mmol) of 3,4-dihydro- 2H-pyran and 50 ml of dichloromethane stirred at room temperature for 21 hours produced a dark yellow solution. At this time an additional 1.80 g (7.2 mmol) of pyridinium p-toluenesulfonate was added to the solution and it was allowed to stir at room temperature for 19 hours. After aqueous workup, a clear, yellow oil was isolated. Purification by flash chromatography (silica, 5% ethyl acetate in hexane) yielded the title compound as a clear, slightly yellow oil. PMR ($CDCl_3$):d 1.38 (9H, s), 1.6–2.1 (6H, m), 3.65–3.75 (1H, m), 3.8–3.95 (1H, m), 5.45 (1H, t, J= 2.5 Hz), 7.03 (1H, dd, J= 8.4, 2..0 Hz), 7.13 (1H, d, J= 8.4 Hz), 7.33 (1H, d, J= 2.0 Hz).

4-Bromo-1-(2-tetrahydropyranoxy)benzene (Compound J)

Using the same general procedure as for the preparation of 4-bromo-2-t-butyl-1-(2-tetrahydropyranoxy)benzene (Compound H), but instead using 15.00 g (86.7 mmol) of 4-bromophenol, 2.18 g (8.7 mmol) of pyridinium p-toluenesulfonate and 10.94 g (11.9 ml, 130.1 mmol) of 3,4-dihydro-2H-pyran and 75 ml of dichloromethane produced a clear, slightly yellow oil. Purification by flash chromatography (silica, 5% ethyl acetate in hexane) yielded a mixture of 4-bromophenol and the desired THP-ether. This mixture was separated by diluting with 300 ml of 1N aqueous NaOH solution, stirring at room temperature followed by ether extraction. The organic phase was dried over $K_2CO_3$, filtered and concentrated in vacuo to give the title compound as a white solid. PMR ($CDCl_3$):d 1.5–2.1 (6H, m), 3.5–3.7 (1H, m), 3.8–3.95 (1H, m), 5.37 (1H, t, J= 3.2 Hz), 6.9–6.96 (2H, m), 7.34–7.39 (2H, m).

3-Bromo-1-(2-tetrahydropyranoxy)benzene (Compound K)

To a solution of 8.80 g (50.9 mmol) of 3-bromophenol (distilled) and 1.28 g (5.1 mmol) of pyridinium p-toluenesulfonate in 50 ml of dichloromethane was added 6.42 g (7.0 ml, 76.3 mmol) of 3,4-dihydro-2H-pyran. The resulting clear solution was stirred at room temperature for 24 hours, partitioned between 200 ml of water and 400 ml of hexane, and the layers were separated. The organic phase was washed with 100 ml of water, 50 ml of 1N aqueous NaOH solution and 100 ml of brine solution, dried over $K_2CO_3$, filtered and concentrated in vacuo to a clear, slightly yellow oil. Purification by flash chromatography (silica, 5% ethyl acetate in hexane) yielded the title compound as a white solid. PMR ($CDCl_3$):d 1.55–2.04 (6H, m), 3.55–3.65 (1H, m), 3.8–3.95 (1H, m), 5.40 (1H, t, J= 2.9 Hz), 6.96–7.00 (1H, m), 7.09–7.17 (2H, m), 7.22–7.24 (1H, m).

2-(1-adamantyl)-4-bromo-1-(2-tetrahydropyranoxy)benzene (Compound L)

Using the same general procedure as for the preparation of of 4-bromo-2-t-butyl-1-(2-tetrahydropyranoxy)benzene (Compound H), but instead using 9.17 g (29.9 mmol) of 2-(1-adamantyl)-4-bromophenol (Compound F), 0.75 g (3.0 mmol) of pyridinium p-toluenesulfonate, 3.77 g (4.1 ml, 44.8 mmol) of 3,4-dihydro-2H-pyran and 50 ml of dichloromethane produced a bright yellow solid. Purification by flash chromatography (preabsorbed onto silica with chloroform, eluted with 2% ethyl acetate in hexane) yielded the title compound as a nearly white solid. PMR ($CDCl_3$):d 1.6–2.2 (21H, m), 3.6–3.7 (1H, m), 3.8–3.9 (1H, m), 5.43 (1H, t, J= 2.4 Hz), 7.05 (1H, d, J= 8.7 Hz), 7.23 (1H, dd, J= 8.7, 2.5 Hz), 7.30 (1H, d, J= 2.5 Hz).

2-(1-adamantyl)-5-bromo-1-(2-tetrahydropyranoxy)benzene (Compound M)

Using the same general procedure as for the preparation of of 4-bromo-2-t-butyl-1-(2-tetrahydropyranoxy) benzene (Compound H), but instead using 12.56 g (40.9 mmol) of 2-(1-adamantyl)-5-bromophenol (Compound G), 1.03 g (4.1 mmol) of pyridinium p-toluenesulfonate, 5.16 g (5.6 ml, 61.3 mmol) of 3,4-dihydro-2H-pyran and 50 ml of dichloromethane produced a clear, orange solution. During aqueous workup, the organic phase was washed with 3×150 ml-portions of sat. aqueous $NaHCO_3$ solution to produce a light yellow solid. Purification by flash chromatography (silica, 3% ethyl acetate in hexane) yielded the title compound as a white solid. PMR ($CDCl_3$):d 1.6–2.1 (21H, m), 3.65–3.72 (1H, m), 3.8–3.93 (1H, m), 5.45 (1H, t, J= 2.8 Hz), 7.04–7.08 (2H, m), 7.32 (1H, br s).

2-[[2-t-Butyl-1-(2-tetrahydropyranoxy)]-4-phenyl]acetylene (Compound N)

A sealed tube was purged under a slight vacuum with a stream of argon gas for several minutes. To this tube was added 20 ml of diethylamine (distilled over solid KOH). Under slight vacuum, the solvent was degassed with a stream of argon gas for 2 minutes and then 5.00 g (16.0 mmol) of 4-bromo-2-t-butyl-1-(2-tetrahydropyranoxy)benzene (Compound H) and 0.61 g (3.2 mmol) of cuprous iodide (ground to a powder) were added. The resulting yellow mixture was degassed (as described above) for 3.5 minutes. To the degassed mixture was added 2.33 g (3.3 mmol) of bis(triphenyl)phosphine palladium (II) chloride and 15 ml of diethylamine. The reaction mixture was degassed for 5.5 minutes and then 7.71 g (11.1 ml, 78.5 mmol) of trimethylsilyl acetylene was added. The tube was sealed and then heated in an oil bath at 55° C. for 3 days. The solution turned dark brown and a black solid formed. The solid was filtered over celite, washed with approximately 350 ml of ethyl ether and discarded. The filtrate was washed with 3×150 ml-portions of water and 100 ml of brine solution, dried over $K_2CO_3$, filtered and concentrated in vacuo to a dark brown, viscous oil. Purification by flash chromatography (silica, 1% ethyl acetate in hexane) yielded 2-[2-t-butyl- 1-(2-tetrahydropyranoxy)- 4-phenyl]-1-trimethylsilyl acetylene. The crude TMS-acetylenic compound was dissolved in 35 ml of methanol and 0.16 g (1.2 mmol) of anhydrous potassium carbonate was added to the solution. The solution was allowed to stir at room temperature overnight, concentrated in vacuo, diluted with 35 ml of sat. aqueous $NaHCO_3$ solution and allowed to stir at room temperature for 5 minutes. The solution was extracted with 50 ml of dichloromethane and the layers were separated. The aqueous layer was washed with 3×50 ml-portions of dichloromethane. All organic phases were combined, washed with 100 ml of water and 50 ml of brine solution, dried over $MgSO_4$, filtered and concentrated in vacuo to give an orange solid. Purification by flash chromatography (silica, 5% ethyl acetate in hexane) yielded the title compound as a yellow solid. PMR ($CDCl_3$):d 1.40 (9H, s), 1.6–2.1 (6H, m), 2.98 (1H, s), 3.6–3.7 (1H, m), 3.8–3.9 (1H, m), 5.49 (1H, t, J=2.6 Hz), 7.11 (1H, d, J= 8.5 Hz), 7.31 (1H, dd, J=8.5, 2.1 Hz ), 7.43 (1H, d, J= 2.1 Hz).

2-[[2-t-Butyl-1-(2-tetrahydropyranoxy)]-5-phenyl]acetylene (Compound O)

Using the same general procedure as for the preparation of 2-[[2-t-butyl-1-(2-tetrahydropyranoxy)]- 4-phenyl]acetylene (Compound N), but instead using 10.07 g (32.1 mmol) of 5-bromo-2-t-butyl-1-(2-tetrahydropyranoxy) benzene (Compound I), 1.53 g (8.0 mmol) of cuprous iodide (ground to a powder), 5.64 g (8.0 mmol) of bis(triphenyl)phosphine palladium (II) chloride, 15.79 g (22.7 ml, 160.7 mmol) of trimethylsilyl acetylene and 70 ml of diethylamine (distilled over solid KOH) heated in an oil bath at 55° C. for 43.5 hours produced a brown solution. At this time, an additional 0.78 g (4.1 mmol) of cuprous iodide (ground to a powder), 2.82 g (4.0 mmol) of palladium (II) catalyst and 10.4 ml (73.6 mmol) of TMS-acetylene were added to the mixture. The tube was resealed and heated at 55° C. in an oil bath for 2 days to give a brown oil following aqueous workup. Purification by flash chromatography (preabsorbed onto silica with chloroform, eluted with 5% ethyl acetate in hexane) yielded 2-[[2-t-butyl-1-(2-tetrahydropyranoxy)]-5-phenyl]-1-trimethylsilyl acetylene. The crude TMS-acetylenic compound was converted into the title compound (brown oil) by stirring with 0.78 g (5.7 mmol) of anhydrous potassium carbonate in 100 ml of methanol. Purification by flash chromatography (silica, 3% ethyl acetate in hexane) yielded the title compound as an orange oil. PMR ($CDCl_3$):d 1.40 (9H, s), 1.6–2.1 (6H, m), 3.01 (3H, s), 3.6–3.7 (1H, m), 3.8–3.95 (1H, m), 5.47 (1H, t, J= 2.7 Hz), 7.06 (1H, dd, J= 8.0, 1.7 Hz), 7.22 (1H, d, J= 8.0 Hz), 7.31 (1H, d, J= 1.7 Hz).

2-[[1-(2-Tetrahydropyranoxy)]-4-phenyl]acetylene (Compound P)

Using the same general procedure as for the preparation of 2-[[2-t-butyl-1-(2-tetrahydropyranoxy)]- 4-phenyl]acetylene (Compound N), but instead using 10.00 g (38.9 mmol)

of 4-bromo-1-(2-tetrahydropyranoxy)benzene (Compound J), 1.48 g (7.8 mmol) of cuprous iodide (ground to a powder), 6.28 g (8.9 mmol) of bis(triphenyl)phosphine palladium (II) chloride, 19.10 g (27.5 ml, 194.5 mmol) of trimethylsilyl acetylene and 60 ml of diethylamine gave a dark brown solid. Purification by flash chromatography (preabsorbed onto silica with chloroform, eluted with 2% ethyl acetate in hexane) yielded 2-[[1-(2-tetrahydropyranoxy)] -4-phenyl]-1-trimethylsilyl acetylene. The crude TMS-acetylenic compound was converted into the title compound (brown solid) by stirring with 0.54 g (3.9 mmol) of anhydrous potassium carbonate in 50 ml of methanol. Purification by flash chromatography (silica, 3% ethyl acetate in hexane) yielded the title compound as a yellow oil. PMR (CDCl$_3$):d 1.55–2.1 (6H, m), 3.00 (1H, s), 3.55–3.7 (1H, m), 3.8–3.95 (1H, m), 5.37 (1H, t, J= 3.0 Hz), 6.92–7.00 (2H, m), 7.35–7.4 (2H, m).

2-[[1-(2-Tetrahydropyranoxy)]-3-phenyl]acetylene (Compound Q)

Using the same general procedure as for the preparation of 2-[[2-t-butyl-1-(2-tetrahydropyranoxy)]- 4-phenyl]acetylene (Compound N), but instead using 5.00 g (15.6 mmol) of 3-bromo-1-(2-tetrahydropyranoxy)benzene (Compound K), 0.74 g (3.9 mmol) of cuprous iodide (ground to a powder), 2.73 g (3.9 mmol) of bis(triphenyl)phosphine palladium (II) chloride, 4.58 g (6.6 ml, 46.7 mmol) of trimethylsilyl acetylene and 30 ml of diethylamine produced a brown solid. Purification by flash chromatography (preabsorbed onto silica with chloroform, eluted with 3% ethyl acetate in hexane) gave 2-[[1-(2-tetrahydropyranoxy)]-3-phenyl]-1-trimethylsilyl acetylene as a light yellow solid. The crude trimethylsilyl acetylene was converted into the title compound (brown solid) by stirring with 0.78 g (5.6 mmol) of anhydrous potassium carbonate in 60 mL of methanol. Purification by flash chromatography (silica, 2% ethyl acetate in hexane) yielded the title compound as a tan solid. PMR (CDCl$_3$):d 1.6–2.1 (6H, m), 3.05 (1H, s), 3.63–3.7 (1H, m), 3.8–3.95 (1H, m), 5.41 (1H, t, J= 3.1 Hz), 7.03–7.07 (1H, m), 7.10–7.14 (1H, m), 7.19–7.25 (2H, m).

2-[[2-(1-adamantyl)-1-(2-tetrahydropyranoxy)]-5-phenyl]- 1-trimethylsilyl acetylene (Compound R)

A sealed tube was purged under a slight vacuum with a stream of argon gas for several minutes. To this tube was added 25 ml of triethylamine (distilled over solid KOH). Under slight vacuum, the solvent was degassed with a stream of argon gas for 5 minutes and then 5.00 g (12.8 mmol) of 2-(1-adamantyl)-5-bromo-1-(2-tetrahydropyranoxy)benzene (Compound M), 0.50 g (2.6 mmol) of cuprous iodide (ground to a powder) and 25 ml of triethylamine were added. The resulting yellow mixture was degassed (as described above) for 5 minutes. To the degassed mixture was added 1.79 g (2.6 mmol) of bis(triphenyl)phosphine palladium (II) chloride and 25 ml of triethylamine. The reaction mixture was degassed for 5 minutes and then 3.77 g (5.4 ml, 38.3 mmol) of trimethylsilyl acetylene was added. The tube was sealed and then heated in an oil bath at 70° C. for 2 days. The solution turned dark brown and a black solid formed. The solid was filtered over celite, washed with approximately 400 ml of ethyl ether and discarded. The filtrate was extracted with 3×200 ml-portions of water and 100 ml of brine solution, dried over K$_2$CO$_3$, filtered and concentrated in vacuo to give a brown solid. Purification by flash chromatography (silica, 3% ethyl acetate in hexane) yielded the title compound as a pale yellow solid. PMR (CDCl$_3$):d 0.23 (9H, s), 1.6–2.25 (21H, m), 3.6–3.75 (1H, m), 3.8–3.95 (1H, m), 5.49 (1H, t, J= 2.8 Hz), 7.05 (1H, dd, J= 8.1, 1.6 Hz), 7.13 (1H, d, J= 8.1 Hz), 7.26 (1H, d, J= 1.6 Hz).

2-[]2-(1-adamantyl)-1-(2-tetrahydropyranoxy)]-5-phenyl]acetylene (Compound S)

To a solution of 4.17 g (10.2 mmol) of 2-[[2-(1-adamantyl)- 1-(2-tetrahydropyranoxy)]-5-phenyl]-1-trimethylsilyl acetylene (Compound R) in 80 ml of methanol was added 0.28 g (2.0 mmol) of anhydrous potassium carbonate. The solution was allowed to stir at room temperature overnight (21 hours), concentrated in vacuo, and taken up in 5 ml of dichloromethane. 100 Ml of a saturated aqueous NaHCO$_3$ solution was added and the solution was stirred at room temperature for 10 minutes, diluted with 50 ml of dichloromethane and 100 ml of water, and the layers were separated. The aqueous layer was extracted with 3×50 ml-portions of dichloromethane. All organic phases were combined, washed with 100 ml of water and 50 ml of brine solution, dried over MgSO$_4$, filtered and concentrated in vacuo to a light brown solid. Purification by flash chromatography (silica, 5% ethyl acetate in hexane) yielded the title compound as a yellow solid. PMR (CDCl$_3$):d 1.6–2.2 (21H, m), 3.6–3.75 (1H, m), 3.8–3.95 (1H, m), 5.47 (1H, t, J= 1.8 Hz), 7.08 (1H, dd, J=8.0, 1.6 Hz), 7.16 (1H, d, J= 8.0 Hz), 7.31 (1H, d, J=1.6 Hz)

2-[[2-(1-adamantyl)-1-(2-tetrahydropyranoxy)]-4-phenyl]-1-trimethy acetylene (Compound T)

Using the same general procedure as for the preparation of 2-[ [2-(1-adamantyl)-1-(2-tetrahydropyranoxy)]-5 -phenyl]-1-trimethylsilyl acetylene (Compound R), but instead using 5.34 g (13.7 mmol) of 2-(1-adamantyl) -4-bromo-1-(2-tetrahydropyranoxy)benzene (Compound L), 0.65 g (3.4 mmol) of cuprous iodide (ground to a powder), 2.40 g (3.4 mmol) of bis (triphenyl) phosphine palladium (II) chloride, 6.70 g (9.6 ml, 68.3 mmol) of trimethylsilyl acetylene and 95 ml of diethylamine produced a dark brown, viscous oil. Purification by flash chromatography (preabsorbed onto silica with chloroform, eluted with 3% ethyl acetate in hexane) yielded the title compound as a light yellow solid. PMR (CDCl$_3$):d 0.23 (9H, s), 1.6–2.2 (21H, m), 3.6–3.7 (1H, m), 3.8–3.9 (1H, m), 5.48 (1H, t, J= 2.9 Hz), 7.07 (1H, d, J= 8.5 Hz), 7.26 (1H, dd, J= 8.5, 2.1 Hz), 7.34 (1H, d, J= 2.1 Hz)

2-[[2-(1-adamantyl)-1-(2-tetrahydropyranoxy)]-4-phenyl]acetylene (Compound U)

Using the same general procedure as for the preparation of 2-[[2-(1-adamantyl)-1-(2-tetrahydropyranoxy)]-5-phenyl]acetylene (Compound S) but instead using 5.06 g (12.4 mmol) of 2-[[2-(1-adamantyl)- 1-(2-tetrahydropyranoxy)]-4-phenyl]-1-trimethylsilyl acetylene (Compound T), 0.68 g (5.0 mmol) of anhydrous potassium carbonate and 300 ml of methanol produced a dark yellow foamy solid. Purification by flash chromatography (silica, 3% ethyl acetate in hexane) yielded the title compound as a yellow solid. PMR (CDCl$_3$):d 1.6–2.2 (21H, m), 2.98 (1H, s), 3.6–3.7 (1H, m), 3.8–3.95 (1H, m), 5.49 (1H, t, J= 2.6 Hz), 7.11 (1H, d, J= 8.5 Hz), 7.30 (1H, dd, J= 8.5, 2.1 Hz), 7.37 (1H, d, J= 2.1 Hz)

Ethyl 4-[(1-trimethylsilyl)-2-ethynyl] -benzoate (Compound V)

Using the same general procedure as for the preparation of 2-[ [2-(1-adamantyl)-1-(2-tetrahydropyranoxy)]-5-phenyl]-1-trimethylsilyl acetylene (Compound R), but instead using 23.43 g (84.9 mmol) of ethyl 4-iodobenzoate, 4.04 g (21.2 mmol) of cuprous iodide (ground to a powder), 5.96 g (8.5 mmol) of his (triphenyl)phosphine palladium (II) chloride, 25.01 g (36.0 ml, 254.7 mmol) of trimethylsilyl acetylene and 40 ml of diethylamine produced a dark brown, viscous oil. Purification by flash chromatography (preabsorbed onto silica with chloroform, eluted with 3% ethyl acetate in hexane) yielded the title compound as a yellow solid. PMR (CDCl$_3$):d 0.26 (9H, s), (9H, s), 1.40 (3H, t, J= 7.1 Hz), 4.38 (2H, q, J= 7.1 Hz), 7.52 (2H, d, J= 8.1 Hz), 7.98 (1H, d, J= 8.6 Hz)

Methyl 4-ethynylbenzoate (Compound W)

Using the same general procedure as for the preparation of 2-[[2-(1-adamantyl)-1-(2-tetrahydropyranoxy)]-5-phenyl]acetylene (Compound S) but instead using 1.50 g (6.1 mmol) of ethyl 4-[(1-trimethylsilyl)- 2-ethynyl]benzoate (Compound V), 0.17 g (1.2 mmol) of anhydrous potassium carbonate and 50 ml of methanol produced a yellow solid. Purification by flash chromatography (silica, 3% ethyl acetate in hexane) yielded the title compound as an off-white solid. PMR (CDCl$_3$):d 3.23 (1H, s), 3.93 (3H, s), 7.55 (2H, d, J= 8.4 Hz), 8.00 (2H, d, J= 8.5 Hz).

Ethyl 4-[2-[[2-t-butyl-1-(2-tetrahydropyranoxy)]-4-phenyl]ethyn-1-yl]benzoate (Compound 1)

To a 100 ml 3-necked round bottom flask (fitted with a glass stopper, reflux condenser, and a rubber septum) was added 25 ml of diethylamine (distilled over solid KOH). The solvent was degassed with a vigorous stream of argon gas for several minutes. To this solution was added 2.67 g (10.3 mmol) of 2-[[2-t-butyl- 1-(2-tetrahydropyranoxy)]-4-phenyl]acetylene (Compound N) dissolved in 10 ml of diethylamine, 0.39 g (2.1 mmol) of cuprous iodide (ground to a powder), and 2.72 g (9.8 mmol) of ethyl 4-iodobenzoate (Compound A) dissolved in 5 ml of diethylamine. The resultant yellow solution was degassed for 10 minutes after which 1.67 g (2.4 mmol) of bis(triphenyl)phosphine palladium (II) chloride was added. The solution was cooled to 0° C. and stirred at 0° C. for 30 minutes (the initial 5 minutes of stirring were performed with argon purge). The reaction mixture was allowed to warm to room temperature and then stirred overnight. A salt formed against the walls of the flask. The reaction mixture was filtered through celite, washed with 500 ml of ethyl ether and the celite plug discarded. The filtrate was washed with 4×200 ml-portions of water and 150 ml of brine solution, dried over K$_2$CO$_3$, filtered and concentrated in vacuo to yield a yellow foam. Purification by flash chromatography (silica, 5% ethyl acetate in hexane) followed by recrystallization (methanol) yielded the title compound as beige needles. PMR (CDCl$_3$):d 1.38 (3H, t, J= 7.1 Hz), 1.43 (9H, s), 1.6–2.1 (6H, m), 3.6–3.7 (1H, m), 3.8–3.95 (1H, m), 4.38 (2H, q, J= 7.1 Hz), 5.52 (1H, t, J= 2.5 Hz), 7.16 (1H, d, J= 8.5 Hz), 7.36 (1H, dd, J= 8.5, 2.1 Hz), 7.48 (1H, d, J= 2.1 Hz), 7.57 (2H, d, J= 8.4 Hz), 8.01 (2H, d, J= 8.4 Hz).

4-[2-[[2-t-Butyl-1-(2-tetrahydropyranoxy)]-4-phenyl]ethyn-1-yl]benzoic acid (Compound 2)

To a solution of 2.00 g (4.9 mmol) of ethyl 4-[2-[[2-t-butyl-1-(2-tetrahydropyranoxy)]-4-phenyl]ethyn-1-yl]benzoate (Compound 1) in 80 ml of tetrahydrofuran was added 19.7 ml (9.8 mmol) of LiOH (0.5 M aqueous solution). The yellow, homogeneous solution was allowed to stir at room temperature for 19 hours. The reaction mixture was concentrated in vacuo, partitioned between 100 ml of water and 60 ml of hexane and the layers were separated. The aqueous phase was diluted with 200 ml of ethyl ether, cooled to 0° C. and acidified with 1 N sulfuric acid to an approximate pH of 4–5. The layers were separated and the aqueous layer was discarded. The organic phase was washed once with brine solution, dried over MgSO$_4$, filtered and concentrated in vacuo to yield a white solid. The solid was recrystallized (acetonitrile) to give the title compound as fine, white needles. PMR (CDCl$_3$):d 1.43 (9H, s), 1.6–2.1 (6H, m), 3.6–3.75 (1H, m), 3.8–3.95 (1H, m), 5.52 (1H, br s), 7.17 (1H, d, J= 8.6 Hz), 7.37 (1H, dd, J= 8.6, 2.0 Hz), 7.48 (1H, d, J=2.0 Hz), 7.60 (2H, d, J= 8.6 Hz), 8.07 (2H, J= 8.6 Hz).

Ethyl 6-[ 2-[ [ 2-t-butyl-1-(2-tetrahydropyranoxy)] -4-phenyl]ethyn-1-yl]nicotinate (Compound 3)

Using the same general procedure as for the preparation of ethyl 4-[2-[[2-t-butyl-1-(2-tetrahydropyranoxy)]-4-phenyl]ethyn-1-yl]benzoate (Compound 1), but instead using 2.84 g (11.0 mmol) of 2-[[2-t-butyl-1-(2 -tetrahydropyranoxy)]-4-phenyl]acetylene (Compound N), 0.38 g (2.0 mmol) of cuprous iodide (ground to a powder), 2.76 g (10.0 mmol) of ethyl 6-iodonicotinate (Compound C), 1.61 g (2.3 mmol) of bis(triphenyl)phosphine palladium (II) chloride and 50 ml of diethylamine gave a foamy yellowish-red solid. Purification by flash chromatography (silica, 5% ethyl acetate in hexane) followed by recrystallization (methanol) yielded the title compound as yellow crystals. PMR (CDCl$_3$):d 1.42 (3H, t, J= 7 Hz), 1.42 (9H, s), 1.6–2.1 (6H, m), 3.6–3.75 (1H, m), 3.8–3.95 (1H, m), 4.44 (2H, q, J = 7 Hz), 5.53 (1H, t, J=2.4 Hz), 7.17 (1H, d, J= 8.5 Hz), 7.44 (1H, dd, J= 8.5, 2.0 Hz), 7.54–7.58 (2H, m), 8.26 (1H, dd, J= 8.3, 2.2 Hz), 9.19 (1H, d, J= 2.2 Hz).

6-[2-[[2-t-Butyl-1-(2-tetrahydropyranoxy)]-4-phenyl] ethyn-1-yl]nicotinic acid (Compound 4)

Using the same general procedure as for the preparation of 4-[2-[[2-t-butyl-1-(2-tetrahydropyranoxy)-4-phenyl] ethyn-1-yl] benzoic acid (Compound 2), but instead using 1.90 g (4.7 mmol) of ethyl 6-[2-[ [2-t-butyl -1-(2-tetrahydropyranoxy)] -4-phenyl]ethyn-1-yl]nicotinate (Compound 3), 18.7 ml (9.3 mmol) of LiOH (0.5 M aqueous solution) and 80 ml of tetrahydrofuran gave a yellow-white solid. The solid was recrystallized (acetonitrile) to give the title compound as fine, yellow, needle-like crystals. PMR (DMSO-d$_6$):d 1.41 (9H, s), 1.6–2.0 (6H, m), 3.65–3.8 (2H, m), 5.63 (1H, br s), 7.17 (1H, d, J= 8.9 Hz), 7.47–7.50 (2H, m), 7.74 (1H, d, J= 8.1 Hz), 8.26 (1H, dd, J= 8.1, 2 Hz), 9.05 (1H, d, J= 2 Hz).

Ethyl 6-[2-[[2-t-butyl-1-(2-tetrahydropyranoxy)]-5-phenyl] ethyn-1-yl]nicotinate (Compound 5)

Using the same general procedure as for the preparation of ethyl 4-[2-[[2-t-butyl-1-(2-tetrahydropyranoxy)]-4-phenyl]ethyn-1-yl] benzoate (Compound 1), but instead using 2.21 g (8.6 mmol) of 2-[[ 2-t-butyl-1-(2-tetrahydropyranoxy)]-5-phenyl]acetylene (Compound O), 0.45 g (2.4 mmol) of cuprous iodide (ground to a powder), 2.15 g (7.8 mmol) of ethyl 6-iodonicotinate (Compound C), 1.89 g (2.7 mmol) of bis(triphenyl)phosphine palladium (II) chloride and 45 ml of diethylamine gave an orange foam. Purification by flash chromatography (pre-absorbed onto silica with chloroform, eluted with 10% ethyl acetate in hexane) followed by recrystallization (methanol) yielded the title compound as bright yellow, needles. PMR (CDCl$_3$):d 1.42 (3H, t, J= 7 Hz), 1.42 (9H, s), 1.6–2.1 (6H, m), 3.65–3.8 (1H, m), 3.85–3.95 (1H, m), 4.43 (2H, q, J= 7 Hz), 5.50 (1H, t, J= 2.4 Hz), 7.21 (1H, dd, J= 8.1, 1.7 Hz), 7.29 (1H, d, J= 8.1 Hz), 7.44 (1H, d, J= 1.7 Hz), 7.60 (1H, d, J= 8.2 Hz), 8.29 (1H, dd, J= 8.2, 2.2 Hz), 9.20 (1H, d, J= 2.2 Hz).

Ethyl 4-[2-[[2-t-butyl-1-(2-tetrahydropyranoxy)] -5-phenyl]ethyn-1-yl]benzoate (Compound 6)

Using the same general procedure as for the preparation of ethyl 4-[ 2-[ [ 2-t-butyl-1-(2-tetrahydropyranoxy)]-4-phenyl]ethyn-1-yl] benzoate (Compound 1), but instead using 3.30 g (12.8 mmol) of 2-[ [ 2-t-butyl-1-(2-tetrahydropyranoxy)]-5-phenyl]acetylene (Compound O), 0.44 g (2.3 mmol) of cuprous iodide (ground to a powder), 3.20 g (11.6 mmol) of ethyl 4-iodobenzoate (Compound A), 1.87 g (2.7 mmol) of bis(triphenyl)phosphine palladium (II) chloride and 50 ml of diethylamine produced an orange foam. Purification by flash chromatography (preabsorbed onto silica with chloroform, eluted with 5% ethyl acetate in hexane) followed by recrystallization (methanol) yielded the title compound as light brown clusters. PMR (CDCl$_3$):d 1.40 (3H, t, J= 7.1 Hz), 1.42 (9H, s), 1.6–2.1 (6H, m), 3.6–3.75 (1H, m), 3.85–3.95 (1H, m), 4.38 (2H, q, J= 7.1 Hz), 5.53 (1H, br s ), 7.11 (1H, dd, J= 8.1, 2 Hz), 7.27 (1H, d, J= 8.1 Hz), 7.36 (1H, d, J= 2 Hz), 7.57 (2H, d, J= 8.4 Hz), 8.01 (2H, d, J=8.4 Hz).

4-[ 2-[ [ 2-t-Butyl-1- (2-tetrahydropyranoxy)] -5-phenyl] ethyn-1-yl]benzoic acid (Compound 7)

Using the same general procedure as for the preparation of 4-[ 2-[ [ 2-t-butyl-1-(2-tetrahydropyranoxy)]-4-phenyl] ethyn-1-yl] benzoic acid (Compound 2), but instead using 2.01 g (5.1 mmol) of ethyl 4-[ 2-[ [ 2-t-butyl-1-(2-tetrahydropyranoxy)]-5-phenyl]ethyn-1-yl]benzoate (Compound 6), 10.5 ml (10.5 mmol) of LiOH (1M aqueous solution) and 44 ml of tetrahydrofuran (THF), stirred at room temperature for 48 hours and then refluxed overnight produced a white solid. Purification by flash chromatography (silica, 10% ethyl acetate in hexane followed by 15% methanol in dichloromethane) yielded the title compound as an off-white solid. PMR (DMSO-d$_6$):d 1.39 (9H, s), 1.55– 2.0 (6H, m), 3.6–3.8 (2H, m), 5.64 (1H, t,), 7.14 (1H, dd, J= 8.0, 1.6 Hz), 7.26 (1H, d, J= 1.6 Hz), 7.30 (1H, d, J= 8.0 Hz), 7.62 (2H, d, J= 8.3 Hz), 7.97 (2H, d, J= 8.3 Hz).

6-[ 2-[ [2-t-Butyl-1-(2-tetrahydropyranoxy)]-5-phenyl] ethyn-1-yl]nicotinic acid (Compound 8)

Using the same general procedure as for the preparation of 4-[2-[ [ 2-t-butyl-1-(2-tetrahydropyranoxy)]-4-phenyl] ethyn-1-yl] benzoic acid (Compound 2), but instead using 1.50 g (3.8 mmol) of ethyl 6-[ 2-[ [ 2-t-butyl-1-(2-tetrahydropyranoxy)] -5-phenyl]ethyn-1-yl]nicotinate (Compound 5), 8.0 ml (8.0 mmol) of LiOH (1M aqueous solution) and 32 ml of tetrahydrofuran produced a yellow solid. The solid was recrystallized (acetonitrile) to give the title compound as bright yellow crystals. PMR (DMSO-d$_6$):d 1.40 (9H, s), 1.55–2.0 (6H, m), 3.6–3.8 (2H, m), 5.65 (1H, br s), 7.21 (1H, dd, J= 8, 1.7 Hz), 7.3–7.35 (2H, m), 7.77 (1H, d, J= 8.2 Hz), 8.29 (1H, dd, J= 8.2, 2.2 Hz), 9.06 (1H, d, J= 2.2 Hz).

Ethyl 4-[2-[ [2-(1-adamantyl)-1-(2-tetrahydropyranoxy)] - 4-phenyl] ethyn-1-yl] benzoate (Compound 9)

Using the same general procedure as for the preparation of ethyl 4-[2-[ [2-t-butyl-1-(2-tetrahydropyranoxy)]-4-phenyl] ethyn-1-yl] benzoate (Compound 1), but instead using 2.00 g (5.9 mmol) of 2-[[2-(1-adamantyl)-1-(2-tetrahydropyranoxy)]-4-phenyl]acetylene (Compound U), 0.21 g ( 1.1 mmol ) of cuprous iodide (ground to a powder), 1.49 g (5.4 mmol) of ethyl 4-iodobenzoate (Compound A), 0.87 g (1.2 mmol) of bis(triphenyl)phosphine palladium (II) chloride and 60 ml of triethylamine gave a yellow solid. Purification by flash chromatography (preabsorbed onto silica with chloroform, eluted with 10% ethyl acetate in hexane) yielded the title compound as a creme solid. PMR (CDCl$_3$):d 1.40 (3H, t, J= 7.1 Hz), 1.6–2.2 (21H, m), 3.6–3.75 (1H, m), 3.85–4 (1H, m), 4.38 (2H, t, J=7.1 Hz), 5.52 (1H, t, J= 2.4 Hz), 7.15 (1H, d, J= 8.5 Hz), 7.35 (1H, dd, J= 8.5, 2.1 Hz), 7.43 (1H, d, J=2.1 Hz), 7.56 (2H, d, J= 8.4 Hz), 8.01 (2H, d, J=8.4 Hz).

Ethyl 6-[2-[ [ 2-(1-adamantyl)-1-(2-tetrahydropyranoxy)] - 4-phenyl] ethyn-1-yl] nicotinate (Compound 10)

Using the same general procedure as for the preparation of ethyl 4-[2-[ [2-t-butyl-1- (2-tetrahydropyranoxy)]-4-phenyl] -ethyn-1-yl] benzoate (Compound 1), but instead using 2.15 g (6.4 mmol) of 2-[[2-(1-adamantyl)-1-(2-tetrahydropyranoxy)]-4-phenyl]acetylene (Compound U), 0.22 g (1.2 mmol) of cuprous iodide (ground to a powder), 1.61 g (5.8 mmol) of ethyl 6-iodonicotinate (Compound C), 0.94 g ( 1.3 mmol) of bis(triphenyl)phosphine palladium (II) chloride and 60 ml of triethylamine produced an orange solid. Purification by flash chromatography (preabsorbed onto silica with chloroform, eluted with 5% ethyl acetate in hexane) followed by recrystallization (methanol) yielded the title compound as fine, yellow, star-like clusters. PMR (CDCl$_3$):d 1.42 (3H, t, J= 7.2 Hz), 1.6–2.2 (21H, m), 3.6–3.75 (1H, m), 3.8–3.95 (1H, m), 4.42 (2H, q, J= 7.2 Hz), 5.53 (1H, t, J= 2.6 Hz), 7.16 (1H, d, J= 8.4 Hz), 7.43 (1H, dd, J= 8.4, 2 Hz), 7.51 (1H, d, J= 2 Hz), 7.56 (1H, d, J= 8.2 Hz), 8.26 (1H, dd, J= 8.2, 2 Hz), 9.18 (1H, d, J= 2 Hz).

6-[ 2-[[2-(1-adamantyl)-1-(2-tetrahydropyranoxy)]-4-phenyl] ethyn-1-yl]nicotinic acid (Compound 11)

Using the same general procedure as for the preparation of 4-[2-[ [2-t-butyl-1-(2-tetrahydropyranoxy)]-4-phenyl] ethyn-1-yl] benzoic acid (Compound 2), but instead using 1.05 g (2.2 mmol) of ethyl 6-[2-[ [ 2-(1-adamantyl)-1-(2-tetrahydropyranoxy)]- 4-phenyl]ethyn-1-yl]nicotinate (Compound 10), 6.5 ml (6.5 mmol) of LiOH (1.0 M aqueous solution) and 26 ml of tetrahydrofuran gave a yellow solid. Recrystallization (acetonitrile) yielded the title compound as tan crystalline flakes. PMR (DMSO-d$_6$):d 1.6–2.2 (21H, m), 3.6–3.8 (2H, m), 5.64 (1H, br s), 7.16 (1H, d, J= 8.6 Hz), 7.40 (1H, d, J= 2.0 Hz), 7.47 (1H, dd, J= 8.6, 2.0 Hz), 7.74 (1H, d, J= 8.2 Hz), 8.27 (1H, dd, J= 8.2, 2.2 Hz), 9.05 (1H, d, J=2.2 Hz).

4-[2-[[2-(1-adamantyl)-1-(2-tetrahydropyranoxy)]-4phenyl] ethyn-1-yl]benzoic acid (Compound 12)

Using the same general procedure as for the preparation of 4-[2-[[2-t-butyl-1-(2-tetrahydropyranoxy)]-4-phenyl] ethyn-1-yl] benzoic acid (Compound 2), but instead using 1.45 g (3.0 mmol) of ethyl 4-[ 2-[ [ 2-(1-adamantyl)-1-(2-tetrahydropyranoxy)]- 4-phenyl]ethyn-1-yl]benzoate (Compound 9), 9.0 ml (9.0 mmol) of LiOH (1.0 M aqueous solution) and 46 ml of tetrahydrofuran gave the title compound as a light tan solid. PMR (DMSO-d$_6$):d 1.6–2.2 (21H, m), 3.6–3.8 (2H, m), 5.61 (1H, br s), 7.13 (1H, d, J= 8.6 Hz), 7.35 (1H, d, J= 2.0 Hz), 7.40 (1H, dd, J= 8.6, 2.0 Hz), 7.64 (2H, d, J= 8.6 Hz), 7.95 (2H, d, J= 8.6 Hz).

Ethyl 4-[2-[ [ 1-(2-tetrahydropyranoxy)]-4-phenyl] ethyn-1-yl] benzoate (Compound 13)

Using the same general procedure as for the preparation of ethyl 4-[ 2-[ [ 2-t-butyl-1-(2-tetrahydropyranoxy)]-4-phenyl] ethyn-1-yl] benzoate (Compound 1), but instead using 2.00 g (9.9 mmol) of 2-[[ 1-(2-tetrahydropyranoxy)] -4-phenyl] acetylene (Compound P), 0.38 g (2.0 mmol) of cuprous iodide (ground to a powder), 3.03 g (11.0 mmol) of ethyl 4-iodobenzoate (Compound A), 1.60 g (2.3 mmol) of bis(triphenyl)phosphine palladium (II) chloride and 50 ml of diethylamine gave a reddish-yellow solid. Purification by flash chromatography (pre-absorbed onto silica with chloroform, eluted with 5% ethyl acetate in hexane) followed by recrystallization (methanol) yielded the title compound as fine, white crystals. PMR (CDCl$_3$):d 1.40 (3H, t, J= 7.1 Hz), 1.6–2.1 (6H, m), 3.6–3.7 (1H, m), 3.85–3.95 (1H, m), 4.38 (2H, q, J = 7.1 Hz), 5.46 (1H, t), 7.04 (2H, d, J= 8.8 Hz), 7.48 (2H, d, J= 8.8 Hz), 7.56 (2H, d, J= 8.4 Hz), 8.01(2H, d, J= 8.4 Hz).

Ethyl 6-[ 2-[ [ 1-(2-tetrahydropyranoxy)] -4-phenyl] -ethyn- 1-yl] nicotinate (Compound 14)

Using the same general procedure as for the preparation of ethyl 4-[2-[ [2-t-butyl-1-(2-tetrahydropyranoxy)]-4-phenyl] ethyn-1-yl] benzoate (Compound 1), but instead using 1.75 g (8.7 mmol) of 2-[[ 1-(2-tetrahydropyranoxy)] -4-phenyl] acetylene (Compound P), 0.33 g (1.7 mmol) of cuprous iodide (ground to a powder), 2.63 g (9.5 mmol) of ethyl 6-iodonicotinate (Compound C), 1.40 g (2.0 mmol) of bis (triphenyl) phosphine palladium (II) chloride and 55 ml of triethylamine gave an orange solid. Purification by flash chromatography (preabsorbed onto silica with chloroform, eluted with 5% ethyl acetate in hexane) followed by recrystallization (methanol) yielded the title compound as yellow needles. PMR (CDCl$_3$):d 1.42 (3H, t, J= 7.2 Hz), 1.5–2.1 (6H, m), 3.55–3.7 (1H, m), 3.8–3.95 (1H, m), 4.42 (2H, q, J= 7.2 Hz), 5.47 (1H, t, J= 3.0 Hz), 7.05 (2H, d, J= 8.6 Hz), 7.53–7.57 (2H, m), 8.27 (1H, dd, J= 8.3, 2.2 Hz), 9.19 (1H, d, J=2.2 Hz).

6-[ 2-[ [ 1-(2-tetrahydropyranoxy)] -4-phenyl]ethyn-1-yl] nicotinic acid (Compound 15)

Using the same general procedure as for the preparation of 4-[ 2-[ [ 2-t-butyl-1-(2-tetrahydropyranoxy)]-4-phenyl] ethyn-1-yl] benzoic acid (Compound 2), but instead using 0.48 g (1.4 mmol) of ethyl 6-[ 2-[ [ 1-(2-tetrahydropyranoxy)]-4-phenyl]ethyn- 1-yl]nicotinate (Compound 14), 7.0 ml (7.0 mmol) of LiOH (1M aqueous solution) and 28 ml of tetrahydrofuran gave a yellow solid. Purification by flash chromatography (silica, 10% ethyl acetate in hexane followed by 20% methanol in dichloromethane) followed by recrystallization (acetonitrile) yielded the title compound as fine, tan crystals. PMR (DMSO-d$_6$):d 1.5–2.0 (6H, m), 3.55–3.65 (1H, m), 3.7–3.8 (1H, m), 5.57 (1H, t, J= 2.6 Hz), 7.11 (2H, d, J= 8.8 Hz), 7.59 (2H, d, J= 8.8 Hz), 7.73 (1H, d, J= 8.1 Hz), 8.28 (1H, dd, J= 8.1, 2.1 Hz), 9.05 (1H, d, J= 2.1 Hz).

Ethyl 6-[ 2-[ [1-(2-tetrahydropyranoxy)] -3-phenyl]ethyn-1-yl]nicotinate (Compound 16)

Using the same general procedure as for the preparation of ethyl 4-[ 2-[ [ 2-t-butyl-1-(2-tetrahydropyranoxy)] - 4-phenyl] ethyn-1-yl] benzoate (Compound 1), but instead using 0.60 g (3.0 mmol) of 2-[ [ 1-(2-tetrahydropyranoxy)] -3-phenyl] acetylene (Compound Q), 0.13 g ( 0.7 mmol) of cuprous iodide (ground to a powder), 0.84 g (3.0 mmol) of ethyl 6-iodonicotinate (Compound C), 0.39 g (0.6 mmol) of bis(triphenyl)phosphine palladium (II) chloride and 40 ml of diethylamine gave a creme solid. Purification by flash chromatography (preabsorbed onto silica with chloroform, eluted with 5% ethyl acetate in hexane) followed by recrystallization (methanol) yielded the title compound as yellow needles. PMR (CDCl$_3$):d 1.43 (3H, t, J= 7.1 Hz), 1.6–2.1 (6H, m), 3.6–3.7 (1H, m), 3.8–3.95 (1H, m), 4.43 (2H, q, J= 7.1 Hz), 5.43 (1H, t, J= 2.7 Hz), 7.06–7.12 (1H, m), 7.24–7.36 (3H, m), 7.59 (1H, d, J= 8.1 Hz), 8.29 (1H, dd, J= 8.1, 2 Hz), 9.20 (1H, d, J= 2 Hz).

Ethyl 6-[ 2-[ [ 2-(1-adamantyl)-1-(2-tetrahydropyranoxy)] - 5-phenyl] ethyn-1-yl] nicotinate (Compound 17)

Using the same general procedure as for the preparation of ethyl 4-[2-[ [ 2-t-butyl-1-(2-tetrahydropyranoxy)]-4-phenyl] ethyn-1-yl] benzoate (Compound 1), but instead using 1.00 g (3.0 mmol) of 2-[[ 2-(1-adamantyl)-1-(2-tetrahydropyranoxy)]-5-phenyl]acetylene (Compound 5), 0.14 g (0.7 mmol) of cuprous iodide (ground to a powder), 0.90 g (3.3 mmol) of ethyl 6-iodonicotinate (Compound C), 0.42 g (0.6 mmol) of bis(triphenyl)phosphine palladium (II) chloride and 40 ml of N,N-diisopropylethylamine gave a yellow solid after purification by flash chromatography (preabsorbed onto silica with chloroform, eluted with 5% ethyl acetate in hexane). The solid was recrystallized (methanol) to give the title compound as fine, powdery yellow crystals. PMR (CDCl$_3$):d 1.43 (3H, t, J= 7.1 Hz), 1.6–2.2 (21H, m), 3.65–3.8 (1H, m), 3.85–4 (1H, m), 4.43 (2H, q, J= 7.1 Hz), 5.50 (1H, t, J= 2.8 Hz), 7.21–7.26 (2H, m), 7.44 (1H, br s), 7.62 (1H, d, J= 8.2 Hz), 8.34 (1H, dd, J= 8.2, 2.0 Hz), 9.20 (1H, d, J= 2.0 Hz).

Ethyl 4-[ 2-[ [ 2-(1-adamantyl)-1-(2-tetrahydropyranoxy)] - 5-phenyl] ethyn-1-yl] benzoate (Compound 18)

Using the same general procedure as for the preparation of ethyl 4-[ 2-[ [ 2-t-butyl-1-(2-tetrahydropyranoxy)]-4-phenyl] ethyn-1-yl] benzoate (Compound 1), but instead using 1.28 g (3.8 mmol) of 2-[[ 2-(1-adamantyl)-1-(2-tetrahydropyranoxy)]-5-phenyl]acetylene (Compound 5), 0.18 g (1.0 mmol) of cuprous iodide (ground to a powder), 1.17 g (4.3 mmol) of ethyl 4-iodobenzoate (Compound A), 0.54 g (0.8 mmol) of bis(triphenyl)phosphine palladium (II) chloride and 50 ml of diethylamine gave a white solid after purification by flash chromatography (preabsorbed onto silica with chloroform, eluted with 3% ethyl acetate in hexane). The solid was recrystallized (methanol) to give the title compound as white plates. PMR (CDCl$_3$):d 1.40 (3H, t, J= 7.1 Hz), 1.6–2.2 (21H, m), 3.65–3.8 (1H, m), 3.85–4 (1H, m), 4.38 (2H, q, J= 7.1 Hz), 5.52 (1H, br s), 7.13 (1H, dd, J= 8.2, 2 Hz), 7.21 (1H, d, J= 8.2 Hz), 7.35 (1H, d, J= 2 Hz), 7.57 (2H, d, J= 8.3 Hz), 8.01 (1H, d, J= 8.3 Hz).

6-[ 2-[ [ 2-(1-adamantyl)-1-(2-tetrahydropyranoxy)]-5-phenyl]ethyn-1-yl] nicotinic acid (Compound 19)

Using the same general procedure as for the preparation of 4-[2-[ [2-t-butyl-1-(2-tetrahydropyranoxy)]-4-phenyl] ethyn-1-yl] benzoic acid (Compound 2), but instead using 0.36 g (0.7 mmol) of ethyl 6-[ 2-[ [ 2-adamantyl)-1-(2-tetrahydropyranoxy)]-5-phenyl]ethyn-1-yl]nicotinate (Compound 17), 3.7 ml (3.7 mmol) of LiOH (1.0 M aqueous solution) and 15 ml of tetrahydrofuran produced a yellow solid. The solid was recrystallized (acetonitrile) to yield the title compound as fine, yellow needles. PMR (DMSO-d$_6$):d 1.6–2.2 (21H, m), 3.6–3.8 (2H, m), 5.64 (1H, br s), 7.18–7.34 (3H, m), 7.76 (1H, d, J= 8.2 Hz), 8.28 (1H, dd, J= 8.2, 2 Hz), 9.06 (1H, d, J= 2 Hz).

4-[2-[[1-(2-Tetrahydropyranoxy)]-4-phenyl]ethyn-1-yl] benzoic acid (Compound 20)

Using the same general procedure as for the preparation of 4-[2-[[2-t-butyl-1-(2-tetrahydropyranoxy)]-4-phenyl] ethyn-1-yl]benzoic acid (Compound 2), but instead using 0.47 g (1.4 mmol) of ethyl 4-[2-[[1-(2-tetrahydropyranoxy)] -4-phenyl]ethyn- 1-yl]benzoate (Compound 13), 6.8 ml (6.8 mmol) of LiOH (1M aqueous solution) and 30 ml of tetrahydrofuran gave an off-white solid. The solid was recrystallized (acetonitrile) to yield the title compound as fine, white needles. PMR ( DMSO-d$_6$ ):d 1.5–2.0 ( 6H, m), 3.5–3.6 (1H, m), 3.7–3.8 (1H, m), 5.54 (1H, br s), 7.08 (2H, d, J= 8.6 Hz), 7.53 (2H, d, J= 8.6 Hz), 7.64 (2H, d, J= 8.3 Hz), 7.96 (2H, d, J= 8.3 Hz).

4-[2-[[1-(2-Tetrahydropyranoxy)]-3-phenyl]ethyn-1-yl] benzoic acid (Compound 21)

Using the same general procedure as for the preparation of 4-[2-[[2-t-butyl-1-(2-tetrahydropyranoxy)]-4-phenyl] ethyn-1-yl]benzoic acid (Compound 2), but instead using 0.59 g (1.7 mmol) of ethyl 4-[2-[[1-(2-tetrahydropyranoxy)] -3-phenyl]ethyn 1-yl]benzoate (Compound 24), 16.8 ml (16.8 mmol) of LiOH (1M aqueous solution) and 60 ml of tetrahydrofuran gave a yellow solid. The solid was recrystallized (acetonitrile) to yield the title compound as fine, powdery white crystals. PMR (DMSO-d6):d 1.5–2 (6H, m), 3.5–3.6 (1H, m), 3.8–3.9 (1H, m), 5.55 (1H, br s), 7.10 (1H, dd, J= 8.4, 2.0 Hz), 7.18–7.26 (2H, m), 7.36 (1H, dd, J= 7.9, 7.8 Hz), 7.67 (2H, d, J= 8.3 Hz), 7.97 (2H, d, J= 8.3 Hz).

4-[ 2-[ [ 2-(1-adamantyl)-1-(2-tetrahydropyranoxy)] -5-phenyl]ethyn-1-yl]benzoic acid (Compound 22)

Using the same general procedure as for the preparation of 4-[ 2-[ [ 2-t-butyl-1-(2-tetrahydropyranoxy)]-4-phenyl] ethyn-1-yl] benzoic acid (Compound 2), but instead using 0.40 g (0.8 mmol) of ethyl 4-[ 2-[ [ 2-(1-adamantyl) -1-(2-tetrahydropyranoxy)] - 5-phenyl]ethyn-1-yl]benzoate (Compound 18), 8.2 ml (8.2 mmol) of LiOH (1M aqueous solution) and 25 ml of tetrahydrofuran produced an off-white solid. The solid was recrystallized (acetonitrile) to yield the title compound as fine, white crystals. PMR (DMSO-$d_6$):d 1.5–2.2 (21H, m), 3.6–3.8 (2H, m), 5.63 (1H, br s), 7.14–7.25 (3H, m), 7.65 (2H, d, J= 8.3 Hz), 7.96 (2H, d, J= 8.3 Hz).

6-[ 2-[ [ 1-(2-Tetrahydropyranoxy)]-3-phenyl] ethyn-1-yl] nicotinic acid (Compound 23)

Using the same procedure as for the preparation of 4-[ 2-[ [ 2-t-butyl-1-(2-tetrahydropyranoxy)] -4-phenyl]ethyn-1-yl] benzoic acid (Compound 2), but instead using 0.15 g (0.4 mmol) of ethyl 6-[ 2-[ [ 1-(2-tetrahydropyranoxy)]-3-phenyl] ethyn-1-yl] nicotinate (Compound 16), 4.3 ml (4.3 mmol) of LiOH (1M aqueous solution) and 25 ml of tetrahydrofuran gave a yellow solid. The solid was recrystallized (acetonitrile) to yield the title compound as yellow crystals. PMR (DMSO-$d_6$):d 1.5–2.0 (6H, m), 3.5–3.6 (1H, m), 3.7–3.8 (1H, m), 5.57 (1H, br s), 7.15 (1H, dd, J= 8 , 2 Hz), 7.22–7.32 (2H, m), 7.40 (1H, dd, J= 7.8, 7.8 Hz), 7.89 (1H, d, J= 8.1 Hz), 8.30 (1H, dd, J= 8.1, 1.8 Hz), 9.07 (1H, br s).

Ethyl 4-[ 2-[ [ 1-(2-tetrahydropyranoxy)]-3-phenyl]ethyn-1-yl]benzoate (Compound 24)

Using the same procedure as for the preparation of 4-bromo-2-t-butyl-1-(2-tetrahydropyranoxy)benzene (Compound H), but instead using 0.52 g (2.0 mmol) of ethyl 4-[ 2-[ [ 1-hydroxy] -3-phenyl] ethyn-1-yl] benzoate, 0.06 g (0.1 mmol) of pyridinium p-toluenesulfonate, 0.27 g (0.3 ml, 3.2 mmol) of 3,4-dihydro-2H-pyran and 50 ml of dichloromethane produced a yellow oil. Purification by flash chromatography (silica, 10% ethyl acetate in hexane) performed twice yielded the title compound as a clear, viscous, slightly yellow oil. PMR (CDCl$_3$):d 1.40 (3H, t, J= 7.1 Hz), 1.55–2.1 (6H, m), 3.6–3.7 (1H, m), 3.85–3.95 (1H, m), 4.39 (2H, q, J=7.1 Hz), 5.45 (1H, t, J= 3.1 Hz), 7.04–7.08 (1H, m), 7.16–7.19 (1H, m), 7.18–7.29 (2H, m), 7.58 (1H, d, J=8.3 Hz), 8.02 (2H, d, J= 8.3 Hz).

Methyl 4-[ 2-[ [ 2-(1-adamantyl)-1-(2-tetrahydropyranoxy)]-4-phenyl] ethyn-1-yl]benzoate (Compound 25)

Using the same general procedure as for the preparation of ethyl 4-[2-[ [ 2-t-butyl-1-(2-tetrahydropyranoxy)]-4-phenyl] ethyn-1-yl] benzoate (Compound 1), but instead using 2.29 g (5.8 mmol) of 2-[2-(1-adamantyl)-4-bromo-1-(2-tetrahydropyranoxy)]benzene (Compound L), 0.20 g (1.1 mmol) of cuprous iodide (ground to a powder), 0.85 g (5.3 mmol) of methyl 4-ethynylbenzoate (Compound W), 0.93 g (1.3 mmol) of bis(triphenyl)phosphine palladium (II) chloride and 45 ml of triethylamine gave a yellow solid. Purification by flash chromatography (preabsorbed onto silica with chloroform, eluted with 10 % ethyl acetate in hexane) followed by recrystallization (methanol) yielded the title compound as white crystals. PMR (CDCl$_3$):d 1.6–2.2 (21H, m), 3.6–3.5 (1H, m), 3.8–3.95 (1H, m), 5.52 (1H, t, J= 2.6 Hz), 7.15 (1H, d, J= 8.6 Hz), 7.34 (1H, dd, J= 8.4, 2.1 Hz), 7.43 (1H, d, J= 2.1 Hz), 7.56 (2H, d, J= 8.4 Hz), 8.01 (2H, d, J= 8.4 Hz).

What is claimed is:
1. A compound of the formula

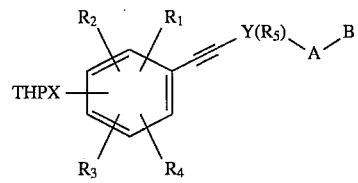

wherein $R_1$–$R_3$ and $R_5$ independently are hydrogen, lower alkyl of 1 to 6 carbons, branched chain alkyl or cycloalkyl of 3 to 15 carbons, lower alkyl substituted cycloalkyl of 3 to 15 carbons;

$R_4$ is branched chain alkyl or cycloalkyl of 3 to 15 carbons, lower alkyl substituted cycloalkyl of 3 to 15 carbons or 2-(1-adamantyl);

THP is a 2-tetrahydropyranyl group;

X is S or O;

Y is a phenyl group substituted with the $R_5$ group defined above;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where $R_7$ is an alkyl group of 1 to 5 carbons, cycloalkyl group of 3 to 5 carbons or alkenyl group of 2 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound of claim 1 wherein X is O.

3. A compound of claim 1 wherein $R_1$–$R_3$ are hydrogen.

4. A compound of claim 1 wherein $R_5$ is hydrogen.

5. A compound of claim 1 wherein the 2-tetrahydropyranoxy substituted phenyl ring is 1,2,4-substituted.

6. A compound of claim 1 wherein the 2-tetrahydropyranoxy substituted phenyl ring is 1,2,5-substituted.

7. A compound of claim 1 where A is $(CH_2)_n$ where n is 0 to 3.

8. A compound of claim 1 where B is COOH or a pharamaceutically acceptable salt thereof, COOR$_8$, or CONR$_9$R$_{10}$.

9. A compound of the formula

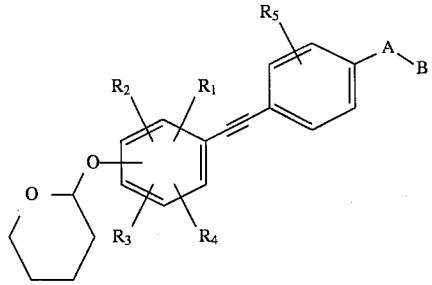

wherein $R_1$–$R_3$ and $R_5$ independently are hydrogen, lower alkyl of 1 to 6 carbons, branched chain alkyl or cycloalkyl of 3 to 15 carbons, lower alkyl substituted cycloalkyl of 3 to 15 carbons;

$R_4$ is branched chain alkyl or cycloalkyl of 3 to 15 carbons, lower alkyl substituted cycloalkyl of 3 to 15 carbons or 2-(1-adamantyl);

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, or $CR_7OR_{13}O$, where $R_7$ is an alkyl group of 1 to 5 carbons, cycloalkyl group of 3 to 5 carbons or alkenyl group of 2 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

10. A compound of claim 9 wherein $R_1$–$R_3$ and $R_5$ are hydrogen.

11. A compound of the formula

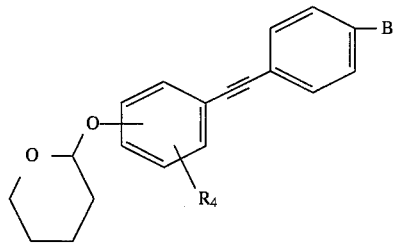

wherein $R_4$ is branched chain alkyl or cycloalkyl of 3 to 15 carbons, lower alkyl substituted cycloalkyl of 3 to 15 carbons or 2-(1-adamantyl), and B is $COOR_8$, or COOH or a pharmaceutically acceptable salt thereof.

12. A compound of claim 11 wherein $R_4$ is t-butyl.

13. A compound of claim 12 wherein the 2-tetrahydropyranoxy group is in the 1-position, the t-butyl group is in the 2-position and the ethynyl group is in the 4-position of the phenyl ring.

14. A compound of claim 13 where B is $COOC_2H_5$, or COOH or a pharmaceutically acceptable salt thereof.

15. A compound of claim 12 wherein the 2-tetrahydropyranoxy group is in the 1-position, the t-butyl group is in the 2-position and the ethynyl group is in the 5-position of the phenyl ring.

16. A compound of claim 15 where B is $COOC_2H_5$ or COOH or a pharmaceutically acceptable salt thereof.

17. A compound of claim 11 wherein $R_4$ is 2-(1-adamantyl).

18. A compound of claim 17 wherein the 2-tetrahydropyranoxy group is in the 1-position, the 2-(1-adamantyl) group is in the 2-position and the ethynyl group is in the 4-position of the phenyl ring.

19. A compound of claim 18 where B id $COOC_2H_5$, $COOCH_3$, or COOH or a pharmaceutically acceptable salt thereof.

20. A compound of claim 17 wherein the 2-tetrahydropyranoxy group is in the 1-position, the 2-(1-adamantyl) group is in the 2-position and the ethynyl group is in the 5-position of the phenyl ring.

21. A compound of claim 20 wherein B is $COOC_2H_5$.

* * * * *

UNITED STATES PATENT AND TRADEMARK OFFICE
CERTIFICATE OF CORRECTION

PATENT NO. : 5,534,641
DATED : July 9, 1996
INVENTOR(S) : Song et al.

It is certified that error appears in the above-indentified patent and that said Letters Patent is hereby corrected as shown below:

Column 2, line 23, "R10" should be --$R_{10}$--;

Column 8, line 23, "(pph$_3$)" should be --(PPh$_3$)--;

Column 18, line 63, "his" should be --bis--;

Column 20, line 25, before "-4-phenyl" please insert --]--;

Column 22, line 29, "4phe" should be --4-phe--;

Column 24, line 62, "-d6" should be -- -$d_6$--;

Column 18, line 1, "2-[]2-" should be --2-[[2- --;

Column 19, line 2, please delete second occurence of "(9H, s),".

Signed and Sealed this

Thirtieth Day of September, 1997

Attest:

BRUCE LEHMAN

Attesting Officer

Commissioner of Patents and Trademarks